United States Patent [19]
Lengfelder

[11] Patent Number: 5,250,257
[45] Date of Patent: Oct. 5, 1993

[54] PROCESS FOR THE STERILIZATION OF IMPLANTS

[75] Inventor: Edmund Lengfelder, Munich, Fed. Rep. of Germany

[73] Assignee: adatomed Pharmazeutische und medizintechnische Gesellschaft mbH, Munich, Fed. Rep. of Germany

[21] Appl. No.: 779,187

[22] Filed: Oct. 22, 1991

[51] Int. Cl.$^5$ .................................. A61L 2/00
[52] U.S. Cl. ........................................ 422/22; 422/21
[58] Field of Search .............. 422/22, 186, 186.04, 422/186.05, 1, 21; 250/492.1, 492.3; 204/193

[56] References Cited

U.S. PATENT DOCUMENTS

| | | | |
|---|---|---|---|
| 2,738,429 | 3/1956 | Goldblith | 422/22 |
| 3,453,196 | 7/1969 | Sporek | 204/193 |
| 3,779,706 | 12/1973 | Nablo | |
| 4,500,791 | 2/1985 | Beisswenger | 250/492.3 |
| 5,041,133 | 8/1991 | Sayano et al. | 623/6 |

FOREIGN PATENT DOCUMENTS 2013460  1/1990  Japan .

OTHER PUBLICATIONS

Block, Disinfection, Sterilization and Preservation, Philadelphia, Pa., Lea & Febiger, 1983, pp. 89-90.

*Primary Examiner*—Michael G. Wityshyn
*Assistant Examiner*—William H. Beisner
*Attorney, Agent, or Firm*—Keck, Mahin & Cate

[57] ABSTRACT

A process for the sterilization of implants made of thermolabile and radio-sensitive materials, particularly intraocular lenses, in which process the sterilizing treatment is performed with alpha or beta rays.

4 Claims, 1 Drawing Sheet

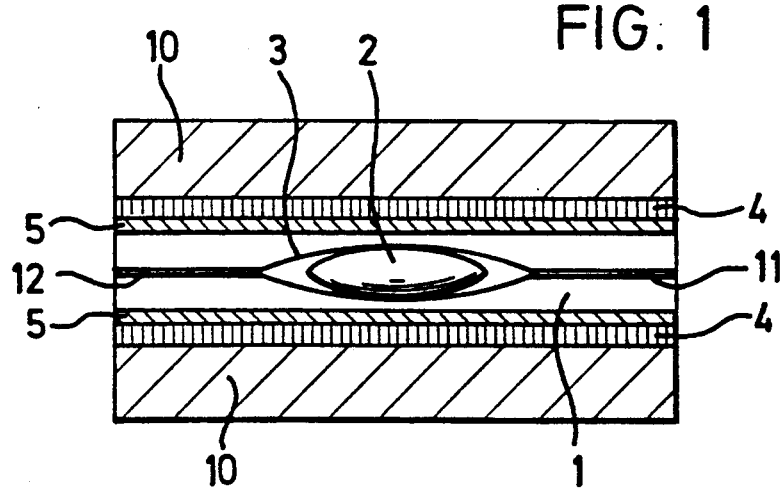
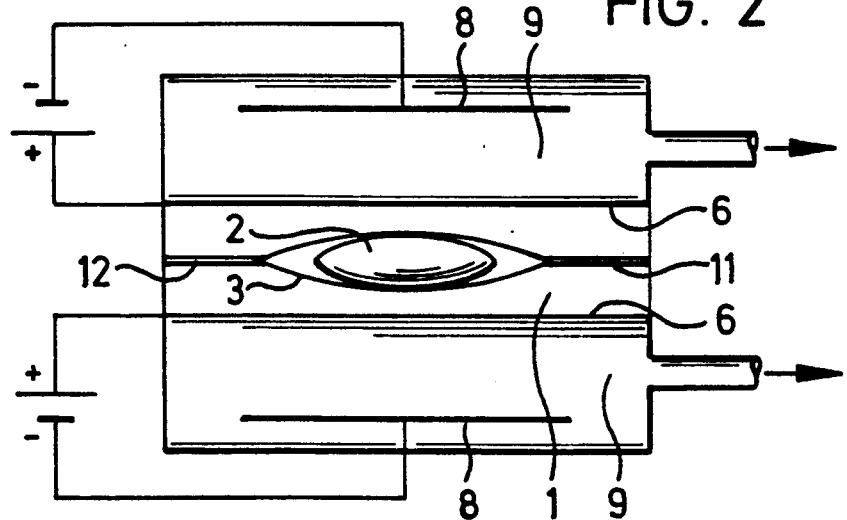
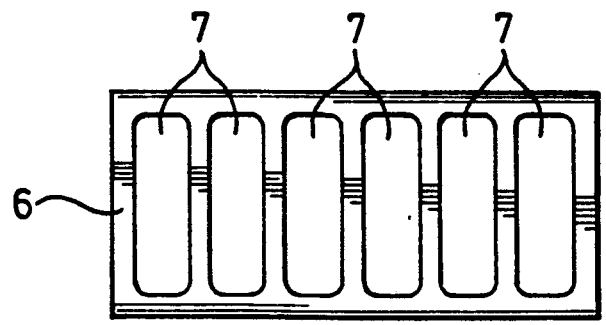

PROCESS FOR THE STERILIZATION OF IMPLANTS

FIELD OF THE INVENTION

The invention relates to a process and an apparatus for the sterilization of implants made of thermolabile and radio-sensitive materials, particularly intraocular lenses.

BACKGROUND OF THE INVENTION

Implants intended for implantation in the human body are frequently made of thermoplastics, such as polymethylmethacrylate, polypropylene, polyethylene, and other materials which cannot be sterilized by either heating or by autoclaving. The sterilization process currently employed for thermolabile objects is that of gas absorption with ethylene oxide. To be sure, the use of ethylene oxide is associated with a high degree of risk, inasmuch as this sterilizing agent is a carcinogen, exhibits a high general potential for toxicity, and is subject to reports of intraocular irritation when used to sterilize intraocular lens implants. Ethylene oxide can thus induce serious toxic systemic effects when used to sterilize an implant, if the gas absorbed by the biomaterial of the implant and the reaction products (chlorohydrine) arising from reaction with water are not quantitatively removed from the biomaterial; due to its high toxicity, ethylene oxide also represents a serious pollutant. Despite these risks, ethylene oxide is routinely used to sterilize thermolabile pharmaceutical agents and thermolabile biomaterials, such as implants, stitching material, operating accessories, etc., since it is currently the only sure method for sterilizing these kinds of thermolabile materials.

Previously employed processes, e.g. sterilization with 10% sodium hydroxide (wet sterilization), have proven to be unreliable. In the case of sterilization of intraocular lenses of polymethylmethacrylate (PMMA), two serious epidemic intraocular infections arose in the United States in 1978, one from mushroom-contaminated sodium hydroxide and another from neutralizing solution contaminated with Pseudomonas. Due to this series of infections, the US health agency, the FDA, has permitted only the gas sterilization of intraocular lenses. There remains considerable uncertainty, however, concerning the quantity of residual ethylene oxide in the treated material. In the case of intraocular lenses the FDA permits a residual content for ethylene oxide and chlorohydrine of 25 ppm per lens for either substance. The French health authority sets the maximum residual content for ethylene oxide at 2 ppm per lens. The German Federal Office of Health recommends a limiting value of 1 ppm for ethylene oxide and 150 ppm for chlorated ethylene hydrine as applied to intraocular lenses.

In the alternative use of radio-sterilization employing gamma radiation, the danger arises of a structural modification of the biomaterial, thereby raising questions about the suitability of the radiated implant for the intended medical purpose. Changes occurring in the material call in question the suitability of the implant, particularly when the treated biomaterial is completely penetrated by the gamma rays during treatment. For example, in the case of intraocular lenses, the lenses have relatively thin attachment threads by means of which they are attached to the body at the site of implantation. Gamma radiation creates the danger of rendering these attachment threads brittle, so that they will no longer be able to fulfill their function. In addition, gamma radiation results in darkening and discoloration of the lens material. Due to the high risks associated with radio-sterilization employing gamma rays, high requirements must be met with respect to qualitative change, radiolysis products, storage, and the like. Consequently the conditions demanded for the licensing of radio-sterilization procedures cannot presently be fulfilled for medically employed biomaterial, and the substitution of gamma radiation for ethylene oxide is not currently possible.

SUMMARY OF THE INVENTION

The goal of the invention therefore is to create a process and an apparatus for the sterilization of implants of thermolabile and radio-sensitive materials, particularly intraocular lenses, in which radio-sterilization can be employed safely without altering the functional integrity of the implant material.

This problem is solved by the inventive process initially mentioned in that sterilization treatment is employed using alpha or beta rays which are directed at the implant surface in the form of diffuse radiation.

With the initially mentioned apparatus this problem is solved by the invention in that a sterilization space for the implant being sterilized in provided between at least two diffusely radiating radiation sources in the form of alpha or beta emitters.

For the material in question (with a specific gravity of about 1), alpha radiation with conventional radionuclides has only a slight depth of penetration of up several times 10 micrometers, thus eliminating the danger of uncontrolled structural modification in the biomaterial employed in the implant. At the same time, the alpha radiation provides faultless sterilization, i.e. kills living germs and/or those capable of development. Beta radiation can also be employed when the electron energy is calibrated to an average level on the order of at least $(0.5 \times 10^5)$ eV to about $(2.4 \times 10^5)$ eV, such that the beta radiation does not penetrate too deeply into the biomaterial of the implant, but rather exerts its sterilizing effect on the surface of the implant.

When the invention is employed with intraocular lenses it is important that the lens material not be discolored by radio-sterilization. Since neither the alpha radiation nor the beta radiation to be applied penetrates into the lens material, there is no danger of discoloration. Embrittlement of the material is also avoided.

The invention thus advantageously provides sterilization which avoids the retention of problematic toxic substances and undesirable material alteration.

When alpha emitters are employed, the implants and their envelopes, for example, welding foils, are sterilized separately in a vacuum. Only a fraction (approx. 5 to 20%) of the dose used in beta radiation is required to kill the germs. To be sure, when beta rays are used it is possible to radiate the implants, e.g. intraocular lenses, when they have been welded into the welding foils, which have a thickness of about 0.05 mm—and thus to simultaneously sterilize both the welding foil and the intraocular lens contained within it. A vacuum in the sterilization space is not necessary for beta radiation.

Both with the alpha and the beta radiation the dose applied to the implant surface, which is the site of the germs, is significantly higher than in the radiated material, and the desired sterilizing effect is thus achieved without the material itself being reduced in quality or damaged in its structure.

Radionuclides are suitable as radiation sources, for example Am-241 or Am-243 as an alpha emitter. Suitable as beta emitters are, for example, Tl-204, with an average Gaussian distribution energy of about 240 keV. These radionuclides can be applied in the form of layers on a flat or vaulted support surface, for example a metal plate. Pm-147 is also a suitable beta emitter. Particularly in the case of nuclides emitting beta rays, for example Sr-90/Y-90, a protective foil, e.g. of a precious metal, with a thickness of 0.02 mm, can be applied above the nuclide layer. This foil also serves as a dispersing foil which reduces the electron energy with its total mass stopping power and thus also reduced the penetration depth of the electrons into the implant.

The emitter area is roughly adapted to that of a welding bag or other cladding in which the intraocular lens or implant is positioned. Two emitter areas will preferably be employed, which face each other at a distance about 1 cm. This arrangement provides a 4 pi geometry. The welding bags containing the objects to be sterilized are transported with conveyor devices or metal devices to the area between the emitters. The total radiation protection needed can be provided by a sheet metal cladding around the apparatus.

The sterilization process of the invention is suitable for all objects that are not hollow bodies and whose surfaces need to be freed of germs.

The dose is adjusted according to the type of germs to be killed. The dose can lie in the range of several krad to several hundred krad. The residence time of the object being sterilized in the sterilization space is adjusted according to the magnitude of the dose.

BRIEF DESCRIPTION OF THE DRAWINGS

The invention will be described in greater detail on the basis of the attached figures. Shown are:
FIG. 1: an initial embodiment of the invention.
FIG. 2: a second embodiment of the invention.
FIG. 3: a portion of the embodiment shown in FIG. 2.

DESCRIPTION OF THE PREFERRED EMBODIMENTS

In the embodiment shown in FIG. 1, radionuclide layers 4 are used as radioactive particle emitters. These radionuclides can consist of Am-241 or Am-243 for alpha emitters and Sr-90/Y-90 for beta emitters. The layers can be applied to the surface of a support 10 by means of vapor-metallization or also by means of sintering. A metal plate can serve as the support 10. Particularly in the case of radionuclides emitting beta rays, a protective foil 5, preferably of precious metal, with a thickness of about 0.02 mm, is applied over the emitter layer 4. The two emitters 4 face each other at a distance of about 1 cm and together form a sterilization space 1.

The object to be sterilized, for example, an implant, which in the depicted embodiment is an intraocular lens 2, is positioned within this sterilization space 1. This intraocular lens 2 is positioned in a welding envelope 3. In the case of beta emitters, the object can be sterilized in the welding envelope 3. Here both the welding envelope 3 and the implant body, for example, the intraocular lens 2, are sterilized. In this case it is not necessary to evacuate the sterilization compartment 1.

When alpha emitters are employed as the flat radiation sources 4, the sterilization compartment 1 is evacuated in order to increase the surface dose. Here also the envelope 3 and the object being sterilized, for example, the intraocular lens, are sterilized separately.

FIG. 1 also schematically depicts securing devices 11 and 12, by means of which the welding envelope 3 and the enclosed object are held in the sterilization space 1. These securing devices 11 and 12 can also serve as guide mechanisms for transport of the material through the sterilization space 1. When the envelope 3 containing the object 2 passes through the sterilization space 1, the speed of transport is adjusted to assure that the necessary radiation dose acts on the enclosed object 2 and on the welding envelope 3. Naturally it is also possible to position the envelope 3 and the enclosed object 2 in stationary fashion within the sterilization space 1 during radiation treatment.

In the embodiment shown in FIG. 2 the radiation source for beta rays is a hot cathode 8 which emits beta rays or electrons. The hot cathode 8 is located in a vacuum chamber 9, which is connected to a vacuum pump not shown in greater detail. The hot cathode 8 is attached to a high voltage source so that the necessary electrons (thermionic emission) are released. Employed here is a directly heated wire or band cathode of high-melting metal or a metal body, covered with e.g. alkaline earth oxides, which has been indirectly brought to incandescence by a separate heating wire.

The opposite cathode 8 in located in a window facing or facade 6 through which the emitted electrons pass and enter the sterilization space 1 to take effect on the envelope 3 and the enclosed object 2, particularly the intraocular lens. As with the embodiment of FIG. 1, securing and transport devices 11 and 12 can be provided for the envelope 3 and the enclosed object 2.

In the embodiment of FIG. 3, the window facade 6 is designed so as to exhibit strip-like windows 7 which permit the passage of the electrons (FIG. 3). In this embodiment the object being sterilized is moved by a transport mechanism so that the bars between the windows 7 and the resulting "radiation shadows" do not limit the sterilization performance.

With the embodiments shown in the figures, the surface of the objects brought into the sterilization space is successfully radiated, without the radiation penetrating more deeply into the material, specifically the material of the enclosed body.

The embodiments depict two facing radiation sources of flat design. It is also possible to provide two further radiation sources running vertical to the former ones, so that the sterilization space 1 is bordered not only above and below by radiation sources but also laterally, making only the ends of the sterilization compartment accessible for the transport and securing of the objects being sterilized.

I claim:

1. A process for sterilization of an intraocular lens, comprising:
   providing an intraocular lens comprising a lens material which is thermolabile and radio-sensitive;
   radiating a surface of the lens with alpha rays or beta rays; and
   controlling the ray energy wherein said rays exert a sterilizing effect only on the lens surface without penetrating into the lens material.

2. The process of claim 1, wherein the beta rays employed have an average electron energy in the range of at least $(0.5 \times 10^5)$ eV to about $(2.4 \times 10^5)$ eV.

3. The process of claim 1, wherein radionuclides are employed as radiation sources.

4. The process of claim 1, wherein a hot cathode is employed as a radiation source.

* * * * *